(12) United States Patent
Babin et al.

(10) Patent No.: US 7,274,448 B2
(45) Date of Patent: Sep. 25, 2007

(54) SHORT RANGE LIDAR APPARATUS HAVING A FLAT SPATIAL RESPONSE

(75) Inventors: François Babin, Charlesbourg (CA); Marc Lévesque, St-Augustin-de-Desmaures (CA)

(73) Assignee: Institut National d'Optique, Sainte-Foy, Quebec (CA)

( * ) Notice: Subject to any disclaimer, the term of this patent is extended or adjusted under 35 U.S.C. 154(b) by 173 days.

(21) Appl. No.: 11/240,149

(22) Filed: Sep. 30, 2005

(65) Prior Publication Data
US 2007/0076201 A1 Apr. 5, 2007

(51) Int. Cl.
*G01N 21/00* (2006.01)
(52) U.S. Cl. .................. 356/342; 356/336; 356/337
(58) Field of Classification Search ........ 356/335–343, 356/39, 28.5, 125; 250/573–574, 559.29–55, 250/222.2; 702/3
See application file for complete search history.

(56) References Cited

U.S. PATENT DOCUMENTS

| | | | |
|---|---|---|---|
| 4,052,600 A | 10/1977 | Wertheimer | |
| 4,245,909 A | 1/1981 | Loos | |
| 4,338,030 A | 7/1982 | Loos | |
| 4,768,713 A | 9/1988 | Roper | |
| 5,116,124 A | 5/1992 | Huttmann | |
| 5,241,315 A | 8/1993 | Spinhirne | |
| 5,278,423 A | 1/1994 | Wangler et al. | |
| 5,859,705 A | 1/1999 | Benedetto et al. | |
| 5,880,836 A | 3/1999 | Lonnqvist | |
| 5,896,190 A | 4/1999 | Wangler et al. | |
| 6,819,265 B2 | 11/2004 | Jamieson et al. | |
| 6,862,083 B1 | 3/2005 | McConnell, Sr. et al. | |
| 6,894,768 B2 * | 5/2005 | Caldwell et al. | .............. 356/28 |

FOREIGN PATENT DOCUMENTS

CA 2000049 4/1990

(Continued)

OTHER PUBLICATIONS

Chourdakis, Giorgos et al., "Analysis of the receiver response for a noncoaxial lidar system with fiber-optic output", Applied Optics, May 20, 2002, vol. 41, No. 15, pp. 2715-2723.

(Continued)

*Primary Examiner*—Gregory J. Toatley, Jr.
*Assistant Examiner*—Tri Ton
(74) *Attorney, Agent, or Firm*—Merchant & Gould P.C.

(57) ABSTRACT

A flat spatial response LIDAR apparatus for detecting particles within a short range is provided. The apparatus includes a light source projecting a light beam which is back-scattered by the particles to be detected. The back-scattered light is received, detected and analyzed. A spatial filter spatially filters the received back-scattered light in order to flatten the spatial response of the apparatus, so that a same concentration of particles at any distance within the short range will generate a signal of substantially the same intensity. This is for example accomplished by a properly profiled mask disposed in front of the detector, or a plurality of spatially distributed waveguides. As a result, the LIDAR apparatus can compensate for the $1/r^2$ dependence, or other dependences of the back-scattered light on the distance r.

15 Claims, 4 Drawing Sheets

FOREIGN PATENT DOCUMENTS

| | | |
|---|---|---|
| CA | 2 437 897 A1 | 8/2002 |
| JP | 58-038864 | 3/1983 |
| JP | 62-106347 | 5/1987 |
| WO | WO94/29762 | 12/1994 |
| WO | WO 02/065153 A1 | 8/2002 |

OTHER PUBLICATIONS

Halldorsson, T. et al., "Geometrical form factors for the lidar function", Applied Optics, vol. 17, No. 2, Jan. 15, 1978, pp. 240-244.

Harms, J. et al., "Geometrical compression of lidar return signals", Applied Optics, Apr. 1, 1978, vol. 17, No. 7, pp. 1131-1135.

Harms, J., "Lidar return signals for coaxial and noncoaxial systems with central obstruction", Applied Optics, May 15, 1979, vol. 18, No. 10, 1559-1566.

Miller, D.R. et al., "Atmospheric Stability Effects on Pesticide Drift from an Irrigated Orchard", American Society of Agricultural Engineers, 2000, vol. 43(5), pp. 1057-1059.

Miller, David R. et al. (The Society for Engineering in Agricultural, Food, and Biological Systems), "Remote Measurement of Spray Drift from Orchard Sprayers Using LIDAR", written for presentation at the 2003 ASAE Annual International Meeting, Jul. 27-30, 2003, 8p.

Miller, David R. et al., "Response of Spray Drift from Aerial Applications at a Forest Edge to Atmosphere Stability", Agricultural and Forest Meteorology, 2000, 100 (2000), pp. 49, 50, 58.

Miller, P.C.H., "Spray Drift and its Measurement", In: Matthews, G.A. and Hislop E.C. (eds), Application Technology for Crop Protection, CAB International, Wellingford, UK, pp. 101-103, 110-115, 1993.

Stoughton, Thomas E. et al., "A Comparison of Spray Drift Predilections to Lidar Data", Agricultural and Forest Meteorology, 1997, 88 (1997) pp. 15, 16, 18.

Stute, Uwe et al., "Aspects of temporal and spatial ranging for bistatic submarine lidar", Proceedings of EARSeL-SIG-Workshop LIDAR, Dresden/FRG, Jun. 16-17, 2000, 96-105.

Velotta, Raffaele et al., "Analysis of the receiver response in lidar measurements", Applied Optics, Oct. 20, 1998, vol. 37, No. 30, pp. 6999-7007.

\* cited by examiner

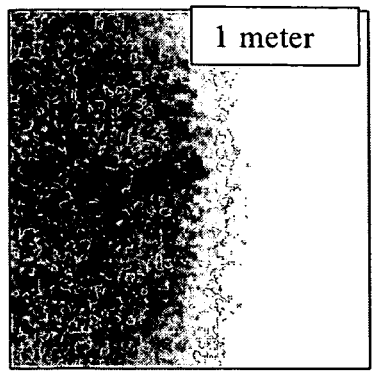
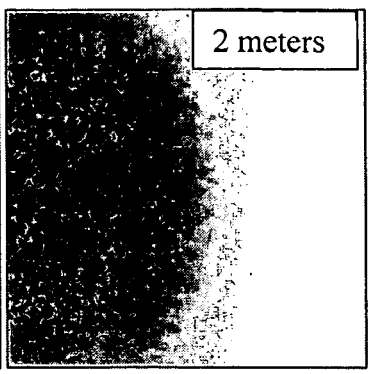
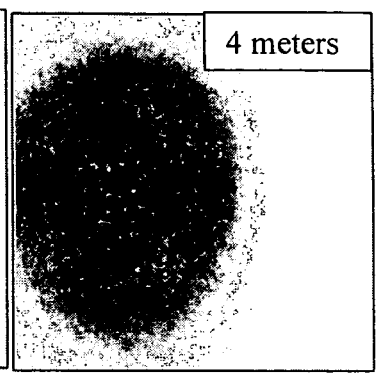
FIG. 3A  FIG. 3B  FIG. 3C
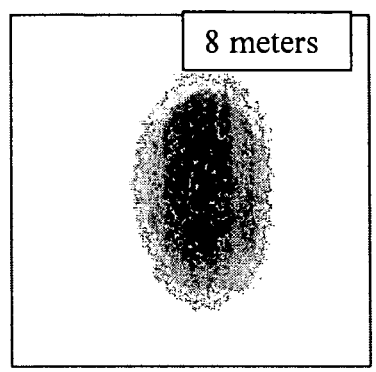
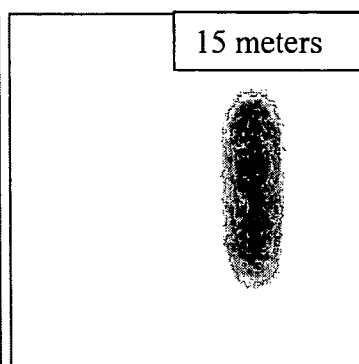
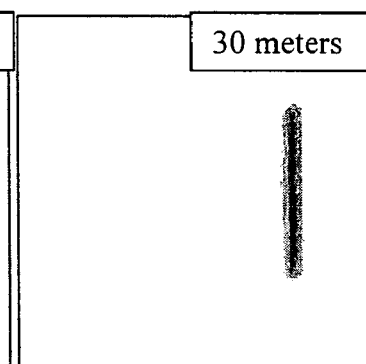
FIG. 3D  FIG. 3E  FIG. 3F
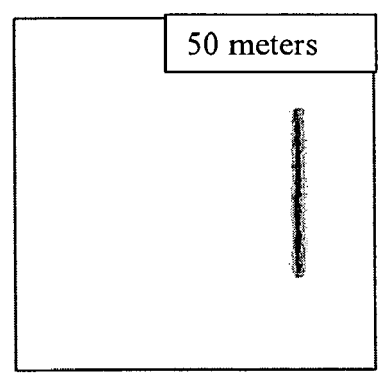
FIG. 3H

SHORT RANGE LIDAR APPARATUS HAVING A FLAT SPATIAL RESPONSE

FIELD OF THE INVENTION

The present invention relates to optical measuring devices and more particularly concerns a LIDAR apparatus with a flat spatial response used for measuring concentrations of particles at a short range.

DESCRIPTION OF THE PRIOR ART

Many industrial fields require the short range detection of particles such as aerosols, fog or clouds of chemical droplets such as pesticides, insecticides and the like. Some also require detection of suspensions, in liquids such as water.

The best known current optical solution for spatially resolved aerosol detection is the use of a LIDAR (Light Detection And Ranging) system. In a LIDAR, a pulsed light signal is sent and is back-scattered by the particles. A temporal and amplitude analysis of the back-scattered light determines the particle concentrations along the path of the emitted beam of light. The scattering phenomena observed by such devices may be instantaneous or delayed according to fluorescent, luminescent or phosphorescent mechanism, and accompanied or not by a wavelength shift. Most particle detection LIDARs are however designed and built for long ranges, usually for 200 meters or more. These highly coherent LIDARs use light beams with very small divergence and detectors with small diameters, of the order of less than 1 mm. This maximizes light collection from long distances (over 1 km) and reduces detection noise levels.

The major impairment of using standard LIDARs for short range applications is the $1/r^2$ dependence of the signal, r being the distance from the target to the receiving optics. For short distances, this entails a huge signal variation; a factor of 10000 (40 dB optical) between 1 m and 100 m, if all the light gathered by the receiving optics falls on the detector. This places stringent requirements on the detection electronics. Moreover, for lower cost operation, the temporal resolution is limited, usually between 10 and 20 nanoseconds, so that a data point represents the average density of aerosols in some volume covering 1.5 to 3 m along the path of the emitted beam. In order to have an accurate value of the average density, the system's spatial response must not vary significantly over the volume along the emitted beam over which the average is taken. A short range LIDAR thus requires that the system response be practically constant over large distances, that is, distances larger than the system's spatial resolution.

For these reasons, what comes to mind to those skilled in the art for measuring particle concentrations in a specific spatial interval is to place a standard LIDAR far enough away from the zone of interest in order to make the measurements in the "long range" mode of operation, the mode for which the spatial response of the LIDAR is practically constant over a distance equivalent to the system's resolution. This is not optimal. These LIDARs are bulky, power hungry and very costly. They were designed for very low light detection. For these applications, an optimized short range LIDAR is desirable.

LIDAR spatial responses are covered in a number of scientific articles, for example:

Giorgos Chourdakis, Alexandros Papayannis and Jacques Porteneuve, "*Analysis of the receiver response for a noncoaxial lidar system with fiber-optic output*", APPLIED OPTICS, 20 May 2002, Vol. 41, No. 15, 2715-2723.

Raffaele Velotta, Bruno Bartoli, Roberta Capobianco, Luca Fiorani, and Nicola Spinelli, "*Analysis of the receiver response in lidar measurements*", APPLIED OPTICS, 20 Oct. 1998, Vol. 37, No. 30, 6999-7007.

J. Harms, "*Lidar return signals for coaxial and noncoaxial systems with central obstruction*", APPLIED OPTICS, 15 May 1979, Vol. 18, No. 10, 1559-1566.

J. Harms, W. Lahmann, and C. Weitkamp, "*Geometrical compression of lidar return signals*", APPLIED OPTICS, 1 Apr. 1978, Vol. 17, No. 7, 1131-1135.

T. Halidorsson and J. Langerhoic, "*Geometrical form factors for the lidar function*", APPLIED OPTICS, Vol. 17, No. 2, 15 Jan. 1978, 240-244.

In these articles the spatial responses of coaxial and non-coaxial systems are described in detail, both with direct detection and through fiber optics. In all these systems, calculations and simulations are for a single field of view (FOV) receiver and a usually round, uniform and unique detection surface. Light distributions in the detection plane are shown. These authors show the spatial variation of the system response without suggesting any equalization scheme, except, to a certain extent, Harms et al. (1978) for a uniaxial system. Harms computes overlap factors and uses them to retrieve and correct measured data, but never for very short ranges (0-100 meters).

Uwe Stute, Michel Lehaitre and Olga Lado-Bordowsky, "*Aspects of temporal and spatial ranging for bistatic submarine lidar*", Proceedings of EARSeL-SIG-Workshop LIDAR, Dresden/FRG, Jun. 16-17, 2000, 96-105, described an underwater LIDAR using multiple field of views, but with independent detection for each FOV. A series of fibers are used, but for purposes unrelated to the equalizing of the spatial response.

U.S. Pat No. 5,880,836 (LÖNNQVIST), entitled "Apparatus and method for measuring visibility and present weather", teaches of a system for measuring particles (fog, rain, snow and cloud ceiling) using a combination of systems. LÖNNQVIST presents a method and apparatus for detecting particles at short range using a pair of detectors in a half-bridge, a beamsplitter and a common lens. This patent however does not tackle the problem of large signal variation with distance for short ranges, nor does it discuss it.

U.S. Pat. No. 5,241,315 (SPINHIRNE), entitled "Micropulse laser radar", describes a low cost, compact, lightweight, reliable and eye safe LIDAR used for atmospheric measurements. SPINHIRNE does point out signal compression because of optical geometry but does not tackle the problem of equalizing the short range spatial response.

Finally, in U.S. Pat. No. 5,116,124 ("Measurement system for scattering of light"), HÜTTMANN describes a uniaxial system, somewhat like that of LÖNNQVIST, capable of short range measurements, but again, without equalization of the response. HÜTTMANN uses multiple fibers, but their purpose is not for equalization of the short range spatial response.

There is therefore a need for a LIDAR apparatus which can be used to measure particle concentrations at a short range and having a generally flat, equalized response in such a range.

SUMMARY OF THE INVENTION

Accordingly, the present invention provides a LIDAR apparatus for measuring concentrations of particles with respect to a distance of these particles from the apparatus within a short range therefrom. The apparatus has a substantially flat spatial response, whereby a same concentration of particles at any distance within the short range will generate a signal of substantially the same intensity.

The apparatus first includes a source optical arrangement projecting an excitation light beam along an optical path. The excitation light beam is back-scattered by the particles within this optical path.

The apparatus further includes a light-collecting arrangement having a field of view intersecting the optical path along the short range. The light-collecting arrangement includes light-receiving optics, receiving the back-scattered light, and a detector detecting the received back-scattered light. The light-collecting arrangement further includes a spatial filter spatially filtering the back-scattered light so as to flatten the spatial response of the apparatus.

The present invention advantageously uses optical propagation after the light-receiving optics and detection geometry to render the response of a LIDAR as flat as possible with respect to distance, for short range detection such as from 1 m to less than 100 m or so. This new class of particle detection LIDARs can be optimized for low cost, low weight, low power consumption, amongst other parameters.

Other features and advantages of the invention will be better understood upon reading of preferred embodiments thereof with reference to the appended drawings.

BRIEF DESCRITION OF THE DRAWINGS

FIGS. 3A to 3H shows the spatial light distribution in a detecting plane for reflecting planes respectively at 1 m (FIG. 3A), 2 m (FIG. 3B), 4 m (FIG. 3C), 8 m (FIG. 3D), 15 m (FIG. 3E), 30 m (FIG. 3F), and 50 m (FIG. 3H).

DESCRIPTION OF PREFERRED EMBODIMENT OF THE INVENTION

Figure 1:
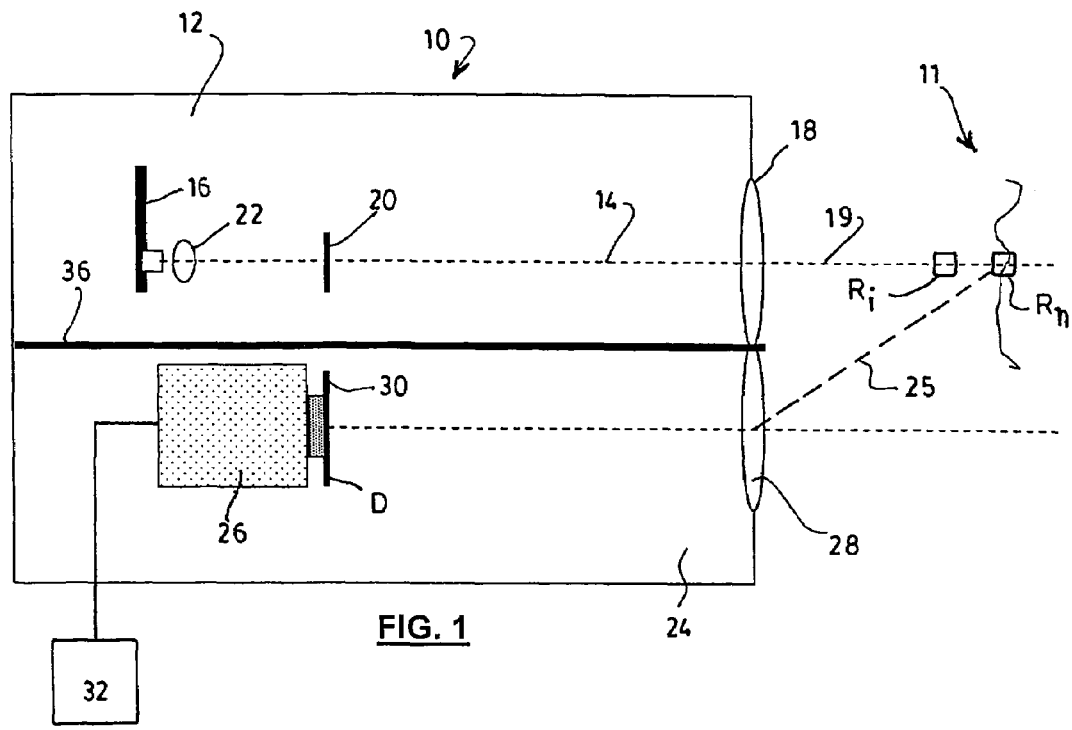
FIG. 1 is a schematic representation of an apparatus according to a preferred embodiment of the invention.

Referring to FIG. 1, there is schematically illustrated a LIDAR apparatus 10 having an almost flat spatial response according to a preferred embodiment of the present invention.

The apparatus is intended for measuring, at short range, concentrations of particles 11 in the air such as aerosols, fog, dust, clouds of chemical droplets such as pesticides, insecticides or the like, or suspensions in a liquid medium, for example in the course of analyzing the turbidity of water in waste water settling tanks.

The term "range" is used herein as referring to the distance between the detected particles 11 and the apparatus 10 itself. It is understood that the designation of "short range" for the apparatus 10 of the invention is by comparison to traditional aerosol detecting LIDAR devices, which are designed to operate at a range of about 200 m or more; in the preferred embodiments, the apparatus 10 is designed to be operated within 100 m, preferably within 50 m. It will of course be understood by a person skilled in the art that the range of the apparatus also has a lower boundary close to the apparatus where the geometry of the system prevents the measure of particle concentrations. Typically, this boundary may for example be around 1 m from the apparatus.

By "flat spatial response", it is understood that a same concentration of particles at any distance within the range of the apparatus will generate a signal of substantially the same intensity. The spatial response of the apparatus may of course deviate slightly from a strict constant value within the target range to a degree determined by the particular needs of a given application.

The apparatus 10 first includes a source arrangement 12 projecting excitation light beam 14, which is preferably pulsed or otherwise modulated. The source arrangement 12 may for example include a pulsed laser source, such as typical low cost sources used for range finders such as for example pulsed high power laser diodes 16 (such as those sold by OSRAM, Perkin-Elmer or Laser Components, for example), a pulsed fiber laser (such as those sold by INO, Keopsys, SPIOptics or OzOptics, for example), a pulsed solid state Q-switched µchip laser (such as those sold by JDS Uniphase, for example) or any other type of pulsed laser generating an appropriate light beam. Preferably, the excitation beam 14 from the source is imaged on a diffuser 20 by an imaging lens 22; this is done in order to render the system eye safe, an important parameter for many short range LIDAR applications. Any other appropriate means may of course be used for such a purpose. An output lens 18 images the light beam from the diffuser 20 along an optical path 19 traversing the target range of the apparatus 10.

The presence of particles 11 in the optical path 19 of the excitation light beam 14 will have the effect of scattering the light beam 14, and a portion 25 thereof will be back-scattered towards the apparatus 10. The term "scattering" is used herein to refer in the large sense to the dispersal of the light beam by the particles as a result of physical interactions therewith. The mechanisms involved may be instantaneous, as is the case for "true" scattering, or according to fluorescent, luminescent or phosphorescent phenomena. Depending on the particular application, the scattering may be without a wavelength change, or accompanied by a small wavelength shift. It will be clear to one skilled in the art that the data processing of the detected light will depend on the type of scattering observed.

For any distance along the optical path 19 of the excitation light beam 14 where back-scattering occurs, there can be said to correspond an elementary scattering volume R delimited by the cross-section of the excitation light beam and a very small distance along the beam. There is therefore a plurality of parallel elementary scattering volumes $R_1$, $R_2 \ldots R_n$ at different distances from the apparatus 10 within its range of operation. The light reaching the apparatus is therefore a mix of the back-scattered light from each scattering volume along the optical path 19.

The apparatus 10 further includes a light collecting arrangement 24 having a field of view intersecting the optical path 19 within the operation range of the apparatus. The light collecting arrangement 24 therefore receives the back-scattered light 25 within its field of view. The light-collecting arrangement 24 includes a detector 26 and light-receiving optics. The light-receiving optics may be embodied by any appropriate optical arrangement. In the illustrated embodiment, it includes an input lens 28 collecting the back-scattered light and propagating it towards at least one detecting plane D.

The distribution of light in any detecting plane varies depending on 1) its distance from the components of the light-collecting arrangement, 2) the elementary scattering volume, or mix of elementary scattering volumes, from which it originates and 3) on the degree of back-scattering from each scattering volume (in other words, in depends on the mix of particles and on their distribution within the excitation beam path). The first factor is fixed for a given system, and the third factor contains the information to be measured by the apparatus. The second factor, however, will be greatly affected by the spatial response of the apparatus, and this effect must be taken into account for the information measured to be significant.

The problematic is best understood through an example. Let us suppose the spatial resolution of the apparatus is 2 m, that is, it is impossible to determine from where a light signal originates within a 2 m long interval along the optical path. At short range, for example between 2 m and 4 m, it is impossible to distinguish between a signal produced by 4000 particles all located in a 1 mm slice around 2 m and a signal produced by 16000 particles in a 1 mm slice around 4 m. If all the light falling on the light collecting arrangement is detected, both signals will be the same, and yet the actual concentrations of particles differ by a factor of 4.

In order to take these short range effects into consideration and obtain accurate concentration values, the relative intensity of light received from each volume $R_i$ if the particle concentration was constant along the optical path has to be tailored. This relative intensity is for example illustrated in FIGS. 3A to 3H, which shows the light distributions in a same detecting plane for different scattering volumes (at different distances from the light collecting arrangement). In this example, the source is a laser diode imaged 50 m away from the apparatus. A scattering target is placed at planes respectively at 1 m, 2 m, 4 m, 8 m, 15 m, 30 m and 50 m from the apparatus, and the resulting back-scattered light is detected in a detection plane at 208 mm from the back of the input lens, which in this case has a 202 mm back focal length. Only the light falling on a 6 mm×6 mm surface is shown. The back-scattered light therefore corresponds to the signal which would originate from different elementary scattering volumes $R_i$ (replaced in this case by scattering surfaces, which is equivalent) within the operation range, all with the same concentration of particles (or the same back-scattering coefficient for the scattering surface). As can be seen, the image from the 50 m reflecting surface (FIG. 3H) is sharp and has substantially the same dimensions as the effective source. Light distributions gathered from other reflecting surfaces are offset from the distribution at 50 m and become larger and larger as the originating surface comes closer to the lenses.

Referring back to FIG. 1, in order to compensate for the aforementioned short range effects, the light-collecting arrangement 24 of the apparatus 10 includes a spatial filter, spatially filtering the back-scattered light 25 to flatten the spatial response of the apparatus. By spatially filtering, it is meant that portions of the light incident on one or more detecting planes is blocked so that only selected portions of the back scattered light 25 is provided to the detector 26. These portions are selected in order for the spatial response of the apparatus to be substantially flat, that is, that a same concentration of particles at any distance within the operation range would generate a signal of substantially the same intensity.

The spatial filter may be embodied by any reflective, refractive or diffractive component or combination thereof accomplishing the desired spatial shaping of the back-scattered light. In the embodiment of FIG. 1, the spatial filter is embodied by a mask 30 disposed along the detecting plane D. The mask 30 preferably has openings therein which allow the above-mentioned selected portions of the back-scattered light therethrough. Alternatively, it may be used in reflection, in which case it may include reflecting and non-reflecting portions thereon defining the filter. In the preferred embodiment, these openings will accept all or a substantial portion of the light from the scattering volume at 50 m from the apparatus, and much less of the light from the scattering volume at 1 m. The proportion of light accepted from 1 m is preferably close to 10000 times smaller than at 50 m, in order to account for the $1/r^2$ dependence.

Figure 4:
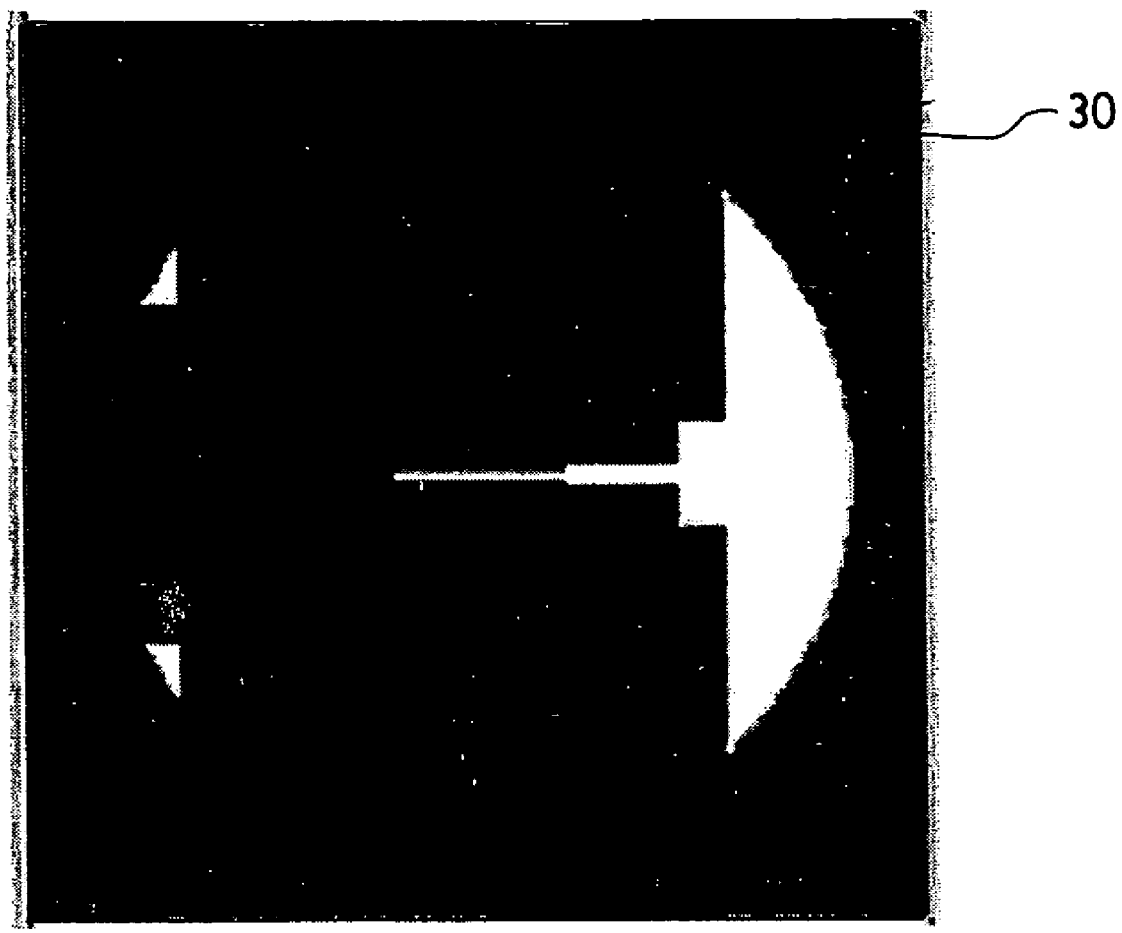
FIG. 4 illustrates the profile of a mask according to one embodiment of the invention.
Figure 5:
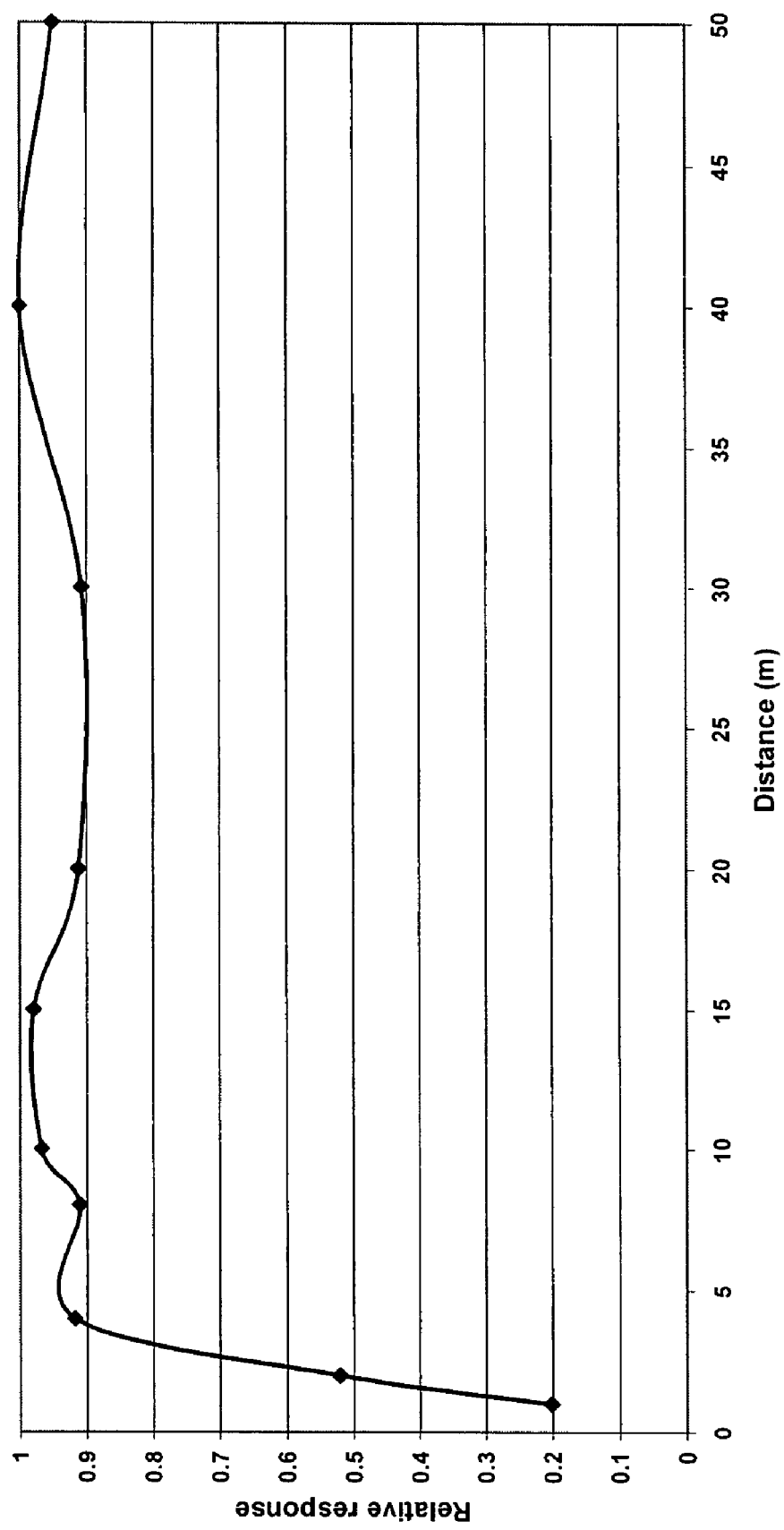
FIG. 5 is a graph illustrating the calculated spatial response of an apparatus according to an embodiment of the invention.

A possible shape for the mask 30 is shown in FIG. 4. The shape accepts the right amount of light from each scattering volume along the optical path of the excitation beam so as to render the system response as flat as possible. A corresponding calculated response is shown in FIG. 5. As can be seen, the obtained response is substantially flat, sufficiently in any event for the needs of most short range applications. As will be readily understood by one skilled in the art, a great number of possible mask profiles could be used to provide the desired result. In order to design the mask, the light distributions in the plane of the mask should preferably be known for a number of reflecting surfaces along the optical path of the emitted beam. The light distributions can be deduced from simulations using optical design software or, preferably, they can be directly measured, for example with a pinhole and detector or with a digital camera. In this latter case, an appropriate optically scattering target is placed at different distances from the emitting lens. A measurement is done for each target distance, by moving the pinhole-detector pair in the mask plane or by acquiring a digital image with the camera detector in the mask plane. Once the light distribution from each target distance is known, as in FIGS. 3A to 3H, computer software may be used to compute the spatial response for a number of different intuitively determined mask geometries until an acceptable design is found. The mask is then fabricated with an appropriate technique (such a laser micro-machining), tested and optimized.

Referring back to FIG. 1, the detector 26 is seen disposed behind the mask 30 and accepts the portions of the scattered light transmitted by this mask. The size of the detector is preferably adapted to the size, shape and configuration of the spatial filter. In this preferred embodiment, the detector 26 is larger than the mask 30. Light impinging on the detector 26 generates an electronic signal that is preferably amplified and digitized in processing electronics 32. The processing electronics 32 should have sufficient bandwidth for the purpose and digitization is done in a proper manner. Various possible hardware and software apt to embody the processing electronics 32 are well known in the art and need not be described further. The result is a set of data points spaced by a time interval corresponding to a distance interval, each data point representing the amount of light back-scattered by a given volume at the data point location.

The apparatus 10 is preferably provided in a casing 34 optically isolating its various components. The source arrangement 12 and light-collecting arrangement 24 are preferably optically isolated from each other by a panel 36.

Figure 2:
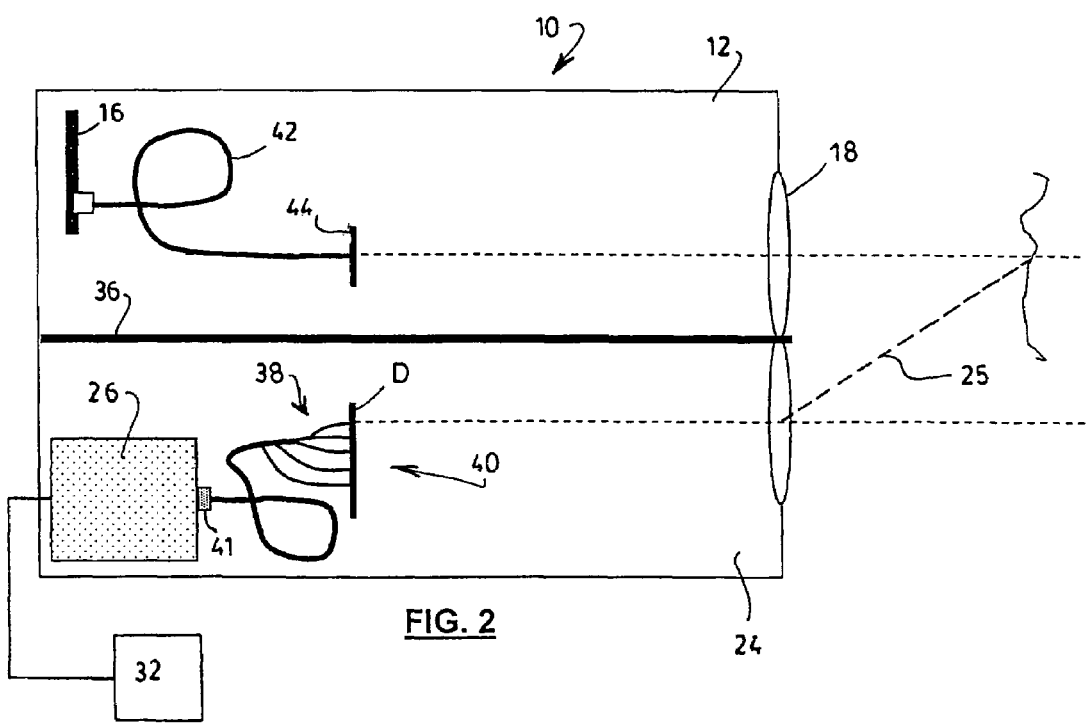
FIG. 2 is a schematic representation of an apparatus according to another preferred embodiment of the invention.

Referring to FIG. 2, there is shown an apparatus 10 according to an alternative embodiment of the present invention. In this embodiment, the source arrangement 12 includes a large core optical fiber 42 to which the laser diode 16 is butt coupled. The optical fiber core has an output 44 which defines a round and uniform source of light. This output 44 is imaged, with output lens 18, at a distance of the apparatus 10 generally corresponding to its operating range (preferably between 50 and 100 m).

In the light-collecting arrangement 24, instead of a mask as described above, the spatial filter is embodied by a plurality of waveguides such as, but not limited to, optical fibers 38, each having an input 40 positioned on one of the detecting planes and an output 41 coupled to the detector 26. The inputs 40 of the fibers 38 are strategically distributed so as to collectively receive the appropriate portions of back-scattered light 25 according to the principle explained above. This ensemble of optical waveguides will therefore preferably accept light in order to compensate for the $1/r^2$ dependence; for example, it will detect all of the light collected from a target scattering volume or surface at 50 m (or another end-of-range target) and much less of the light from the same target at 1 m or less. In any event, the ensemble should accept the right amount of light from any scattering volume so as to render the system response as flat as possible. The inputs 40 of the optical fibers 38 are preferably in the same detecting plane D, but not necessarily. When it is the case, the fibers 38 should all have the same length in order not to distort the time response of the system. The captured portions of the back-scattered light will be guided to reach the detector 26.

Advantageously, the embodiment of FIG. 2 allows a gain of flexibility in the positioning of the detector and associated electronics. In addition, the use of a much smaller detector area improves the signal to noise ratio and lowers the cost of the detector.

It is interesting to note that the different configurations of source optical arrangements and light-collecting arrangements shown in FIGS. 1 and 2 need not be necessarily used in the illustrated combinations. For example, the source optical arrangement of FIG. 2 may be used with the light-collecting arrangement of FIG. 1, and vice versa.

In summary, the present invention provides a useful LIDAR apparatus for detecting particles and measuring substantially accurate concentrations within a shorter range than traditional aerosol detecting LIDARs. It will be noted that one advantage of some of the embodiments of the invention is the reduction of the signal from longer distances than those targeted by the apparatus. The mask can be shaped to receive all of the light from 50 m, but light from 100 m could be reduced by more than the $1/r^2$ dependence, and this reduction could be larger for larger distances between the axes of the output and input lenses. In other words, the apparatus of the present invention can be used to render only a part of the spatial response flat, the other parts falling more or less rapidly to a much lower level. The spatial response can be tailored to the needs of a given application.

It should be clear to one skilled in the art that many modifications could be made to the embodiments described above. Different shapes of light sources are possible, and the mask or detection profile (such as the waveguides of the second embodiment) could be designed in many ways in order to render the system's response as flat as desired for a given application. In addition, the source need not be on the axis of the output lens, lenses need not be of same diameter or focal length and need not be in the same plane.

As for existing LIDARs, these LIDARs could be scanned to form 3-D plots of aerosol, suspension and other particle concentrations.

Of course, numerous modifications could be made to the embodiments described above without departing from the scope of the invention as defined in the appended claims.

The invention claimed is:

1. A LIDAR apparatus for measuring concentrations of particles with respect to a distance of said particles from the apparatus within a short range therefrom, said apparatus having a substantially flat spatial response whereby a same concentration of particles at any distance within said short range will generate a signal of substantially a same intensity, said apparatus comprising:

a source optical arrangement projecting an excitation light beam along an optical path, said excitation light beam being back-scattered by the particles within said optical path; and a light-collecting arrangement having a field of view intersecting said optical path along said short range, said light-collecting arrangement comprising light-receiving optics receiving the back-scattered light and a detector detecting said received back-scattered light, said light-collecting arrangement further comprising a spatial filter spatially filtering said back-scattered light so as to flatten said spatial response of the apparatus.

2. The LIDAR apparatus according to claim 1, wherein said spatial filter comprises a mask disposed in front of said detector, said mask allowing selected portions of the back-scattered light to reach said detector.

3. The LIDAR apparatus according to claim 2, wherein said mask has openings therein allowing said selected portions of the back-scattered light therethrough.

4. The LIDAR apparatus according to claim 1, wherein said spatial filter comprises a plurality of waveguides each having an input receiving said back-scattered light and an output coupled to said detector, the inputs of said waveguides being distributed so as to collectively receive selected portions of the back-scattered light.

5. The LIDAR apparatus according to claim 4, wherein the inputs of the plurality of waveguides are all positioned on a same plane.

6. The LIDAR apparatus according to claim 4, wherein said plurality of waveguides are optical fibers.

7. The LIDAR apparatus according to claim 1, wherein said light-collecting arrangement comprises an input lens receiving said back-scattered light and propagating said light towards said spatial filter.

8. The LIDAR apparatus according to claim 1, wherein said source optical arrangement comprises a modulated light source emitting said excitation light beam.

9. The LIDAR apparatus according to claim 8, wherein said modulated light source is a pulsed laser diode.

10. The LIDAR apparatus according to claim 1, wherein said source optical arrangement comprises an output lens directing the excitation light beam on said optical path.

11. The LIDAR apparatus according to claim 10, wherein said source optical arrangement further comprises means for rendering said excitation light beam eye safe.

12. The LIDAR apparatus according to claim 1, wherein the range of said apparatus is within 100 m.

13. The LIDAR apparatus according to claim 1, wherein the range of said apparatus is within 50 m.

14. The LIDAR apparatus according to claim 1, further comprising processing electronics coupled to said detector for processing a signal generated thereby.

15. The LIDAR apparatus according to claim 1, wherein said spatial filter is designed to compensate for a variation in the back-scattered light inversely proportional to the square of the distance of the particles to the apparatus.

* * * * *